US00PP24093P3

(12) United States Plant Patent

Maillard et al.

(10) Patent No.: US PP24,093 P3

(45) Date of Patent: Dec. 17, 2013

(54) APRICOT TREE NAMED 'ASFCOT0201'

(50) Latin Name: ***Prunus armeniaca* L.**
Varietal Denomination: ASFCOT0201

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 29 days.

(21) Appl. No.: 13/385,650

(22) Filed: Feb. 29, 2012

(65) Prior Publication Data

US 2012/0227140 P1 Sep. 6, 2012

(30) Foreign Application Priority Data

Mar. 2, 2011 (QZ) ..... PBR 20110567

(51) Int. Cl.
*A01H 5/00* (2006.01)

(52) U.S. Cl.
USPC ..... Plt./186

(58) Field of Classification Search
USPC ..... Plt./186
See application file for complete search history.

*Primary Examiner* — Kent L Bell

(74) *Attorney, Agent, or Firm* — Westerman, Hattori, Daniels & Adrian, LLP

(57) ABSTRACT

A new and distinct variety of apricot tree, denominated 'ASFCOT0201', characterized by fruits of very long shelf life without alteration after harvesting, and with a medium orange flesh of high eating quality, aromatic and with a high level of sugar, and with an attractive luminous orange red blush on a luminous orange yellow background.

4 Drawing Sheets

Botanical classification: *Prunus armeniaca* L.
Variety denomination: 'ASFCOT0201'.

This application claims priority of Community plant variety right No. 2011/0567 filed on Mar. 2, 2011, which is hereby incorporated by reference in its entirety.

BACKGROUND OF THE NEW VARIETY

The present invention relates to a new and distinct variety of apricot tree, *Prunus armeniaca* L., which has been given the variety denomination 'ASFCOT0201'. This new tree produces fruit with a long shelf life without alteration after harvesting, very good eating quality, and freestone orange flesh fruit for fresh market in July in the Pyrénées-Orientales department, France. Contrast is made to 'ASFCOT0409' (U.S. Plant Pat. No. 21,135), an apricot tree, for reliable description. 'ASFCOT0201' is a promising candidate for commercial success in that it has very attractive fruits with long shelf life without alteration after harvesting. This new variety results from our plant-breeding program aimed at obtaining apricot trees producing fruits of sweet and aromatic taste, with an attractive bright orange yellow fruit skin covered by an appealing orange red blush. One of our main concerns is also the production of new varieties producing fruits having a long shelf life after harvesting, in order to facilitate long distance shipping. Our final purpose is the production of a range of new apricot tree varieties differing by their time of maturity, while producing fruits of very similar characteristics, in order to provide markets with almost indistinguishable fruits during the whole period of production of apricot.

ORIGIN OF THE VARIETY

The 'ASFCOT0201' apricot tree originated in a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'ASFCOT0201' variety male and female parents are unknown. More particularly, this variety was randomly obtained, from a stone randomly selected and then planted. 'ASFCOT0201' was provisionally designated, tested and genetically identified by a genetic profile, under number 01.20.44 AB ASF 0201 and was registered at the Official Catalogue of the Agriculture Ministry of the French Republic on Nov. 23, 2010 under number 4047128. The 'ASFCOT0201' variety was propagated by grafting on a 'Franc Inra Montclar' (non patented) rootstock. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of apricot tree blooms early in March in the Pyrénées-Orientales department, France. More particularly, it approximately blooms between March 6th and March 15th, generally 3 or 4 days later than 'ASFCOT0409' (U.S. Plant Pat. No. 21,135). 'ASFCOT0201' apricot tree is a non auto-fertile variety; a cross pollination, provided by 'ASFCOT0409' (U.S. Plant Pat. No. 21,135) variety or 'ASFCOT0404' (U.S. Plant Pat. No. 21,138) variety is necessary.

The first fruit of 'ASFCOT0201' apricot tree ripens at the end of June or early in July, generally about 5 days later than 'ASFCOT0409' (U.S. Plant Pat. No. 21,135). However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
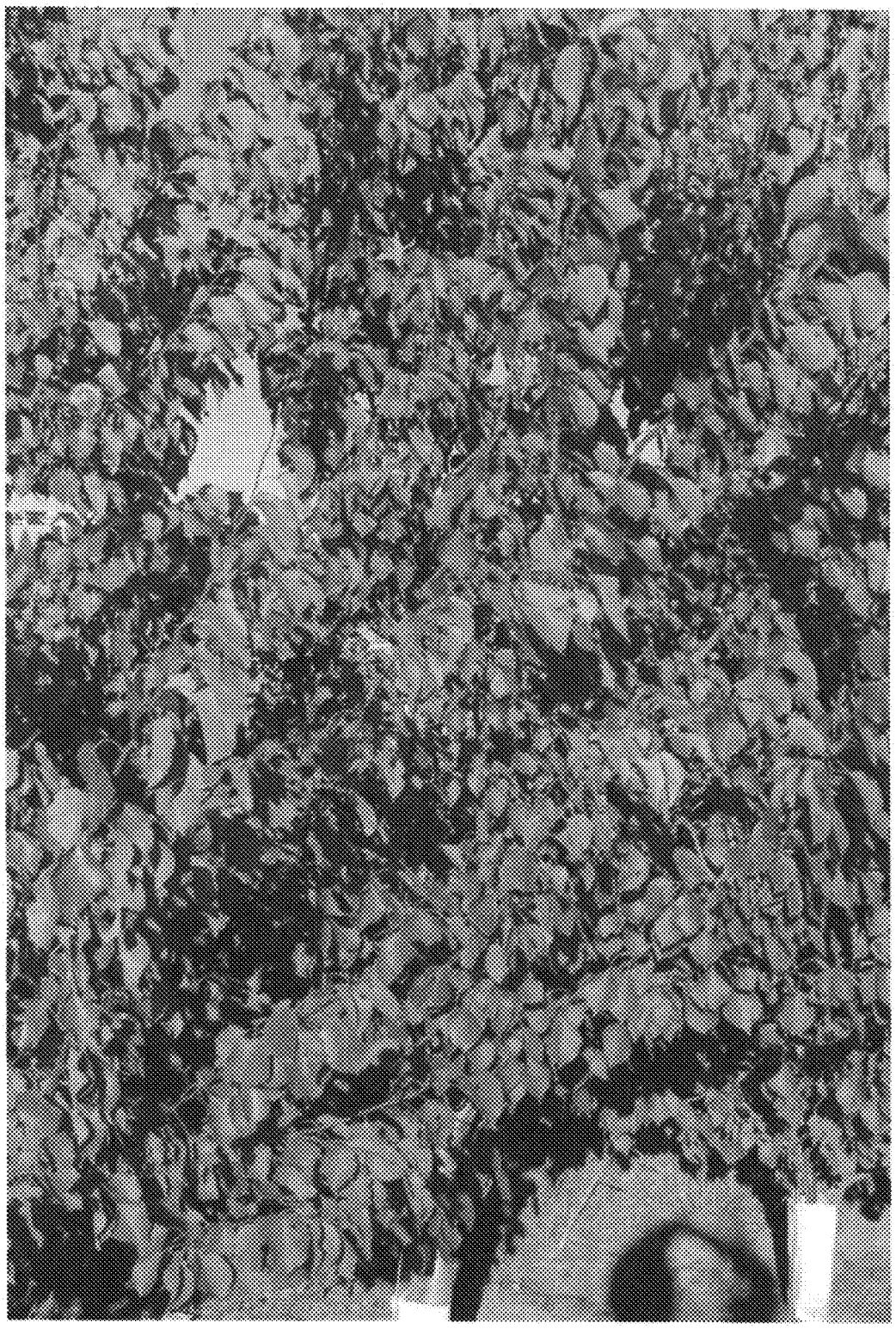
FIG. 1 is a color photograph, which shows a view of a tree of the new variety in orchard, bearing fruits.
Figure 2:
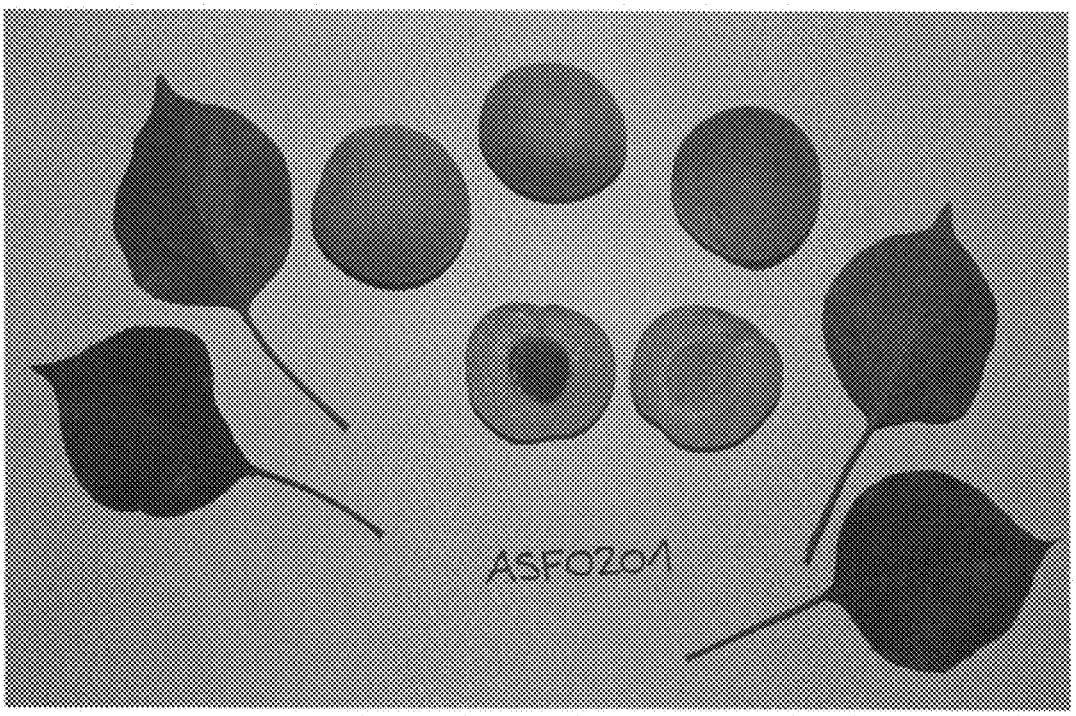
FIG. 2 is a color photograph, which shows three whole fruits and leaves of the new variety, and a fourth fruit, cut in half, with the stone left in one of the halves for depicting the fruit flesh and the stone of the new variety.
Figure 3:
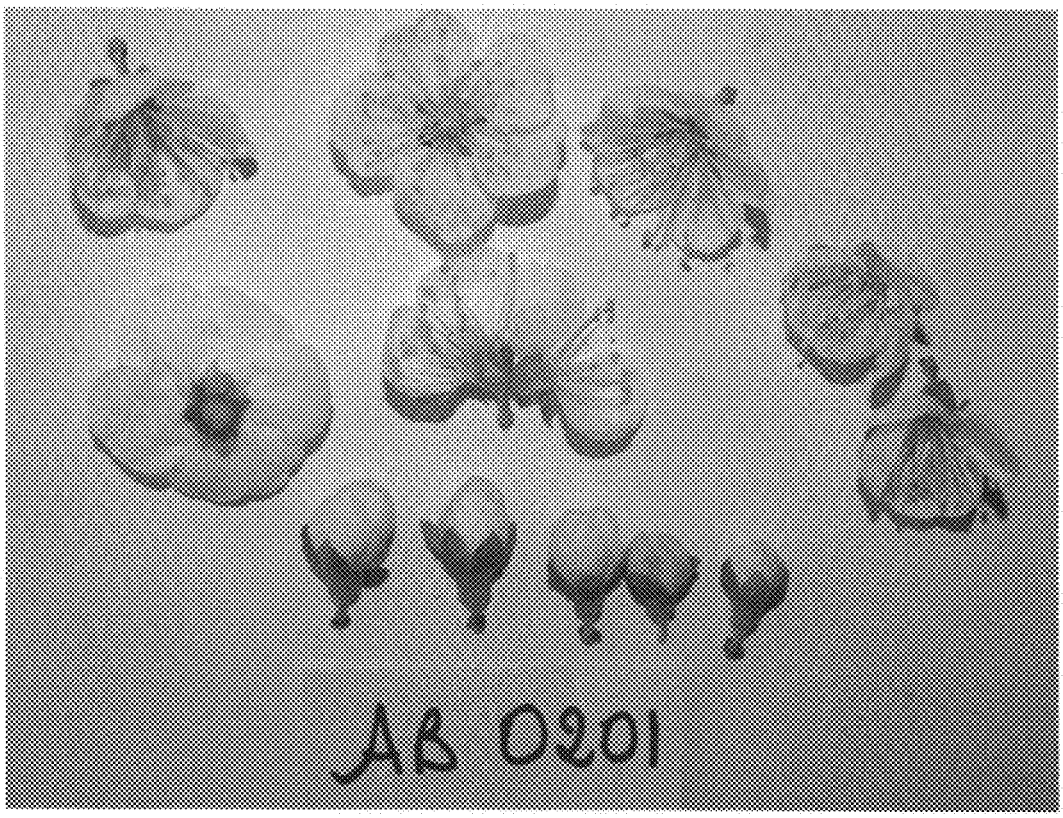
FIG. 3 is a color photograph with reverse and side views of flowers of the new variety, and, with petals removed, reproductive organs of the new variety.
Figure 4:
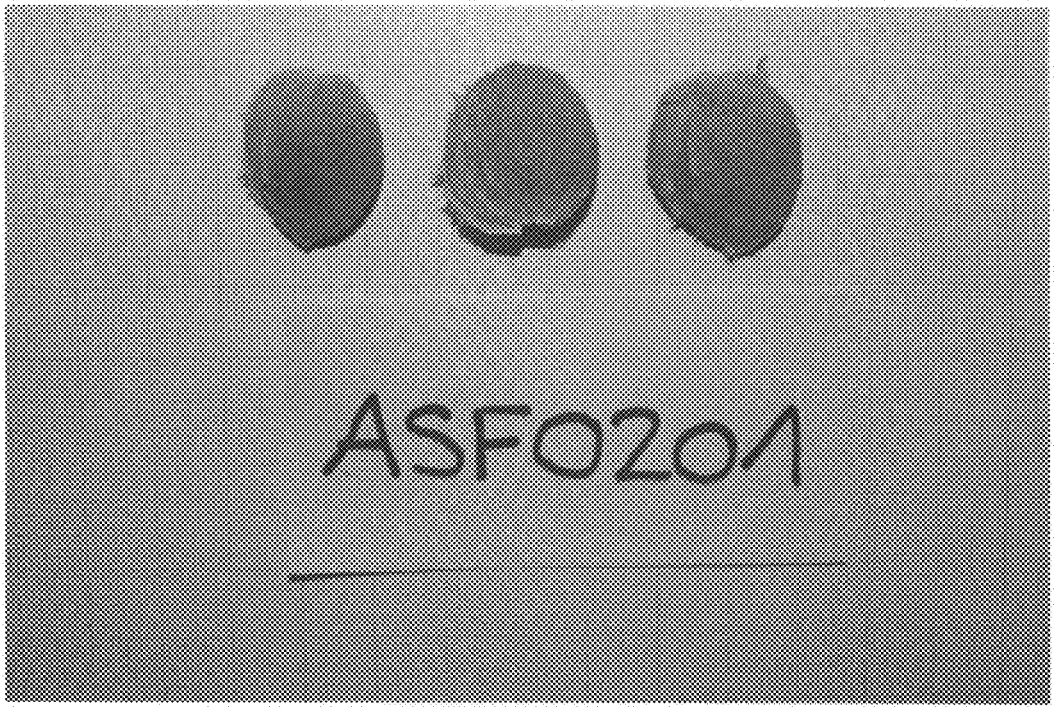
FIG. 4 is a color photograph, which shows different views of the stone.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'ASFCOT0201' is high, due to fruit very long shelf life without alteration after harvesting.

Trees are vigorous and large stature half-standing in a semi-upright out aspect. The time of beginning of flowering is considered medium; flowering begins early in March. The flower petals are very pale pink at the opening, then white. Leaf glands are present and round. Time of maturity for consumption is considered medium. The fruit flesh is considered orange. The fruit skin is medium thick and colored with a red orange blush on an orange yellow background. The stone is medium size. Fruit taste is very aromatic and with a good balance between the level of sugar and acidity.

Compared to 'ASFCOT0409' (U.S. Plant Pat. No. 21,135) apricot tree, 'ASFCOT0201' variety blooms broadly 3 or 4 days later and ripens approximately 5 days later than 'ASFCOT0409', as set forth above. 'ASFCOT0201' variety produces very attractive fruits, with a homogenous presentation and a luminous red coloration, covering 40 to 60% of the fruit skin, on a luminous orange yellow background. The fruit shape of 'ASFCOT0201' is rounder than 'ASFCOT0409' fruits. 'ASFCOT0201' fruits flesh is very tasty, aromatic, with a high level of sugars, and very juicy. The time of maturity of the new variety is also interesting, because it ripens just a few days after 'ASFCOT0409' variety.

DETAILED DESCRIPTION

Referring more specifically to the pomological details of this new and distinct variety of apricot tree, the following was observed on trees in their fourth year of production. under the ecological conditions prevailing at the orchards located near the town of Elne, Pyrénées-Orientales department, France. All observations have been done on rootstock cultivars. Used rootstocks were 'Franc Inra Montclar' (non patented) trees. All major color code designations are by reference to The R.H.S. Color Chart (Fourth Edition) provided by The Royal Horticultural Society of Great Britain.

TREE

Size:

*Generally.*—Considered large as compared to other common commercial apricot cultivars. Trees reach about 250 cm during the first growing season. Trees were pruned during each following season to a height of approximately 250 cm and to a diameter of 200 cm.

Spread: Approximately 200 cm. The whole orchard was oriented to a central leader organization, with tree lines spaced of 4.0 meters and trees spaced of 1.0 meter in a same tree line.

Vigor: Considered vigorous. Current season shoots growth could reach 100 cm. During the first year of growth, trees growth reaches 250 cm. In the second and following seasons, the size of trees is reduced to 250 cm by pruning. However, these characteristics are dependant on soils fertility, cultural practices, and prevailing climatic conditions.

Productivity: Very Productive and regular. Fruit set is spaced by thinning to develop the remaining fruit into the desired market sized fruit. Because of the fruit size, the new variety only requires a medium thinning for the tree valorisation. Thinning was necessary every year during the years of observation. The number of the fruit set varies with the prevailing climatic conditions and cultural practices employed during the bloom period, and is therefore not distinctive of the present variety.

Bearer: Very regular. No alternate bearing was observed.

Form: The 'ASFCOT0201' variety has a naturally semi-upright shape.

Density: Considered highly dense, in order to obtain and observe fruits more quickly.

Fertility: The 'ASFCOT0201' variety is non auto-fertile. A pollination cross, provided by 'ASFCOT0409' (U.S. Plant Pat. No. 21,135) or 'ASFCOT0404 (U.S. Plant Pat. No. 21,138), is necessary.

Hardiness: The present tree was grown and evaluated in France. The variety appears to be hardy under the central Pyrénées-Orientales departmenttypical climatic conditions. Experimentations on different sites with winter chilling requirement comprised between 350 hours and 1200 hours showed a good behaviour of the tree in all cases. The tree also seems to have a good resistance to frosty springtime weather.

TRUNK

Diameter: Approximately between 9.0 cm and 10.0 cm in diameter when measured at a distance of approximately 20 cm above the soil level.

Bark texture: Considered smooth to rough when numerous lenticels are present.

Bark coloration: The bark has a green brown (RHS Brown N 200 B) or a silver-orange brown (RHS Greyed Orange 166A) coloration, depending on the sunlight exposure.

Lenticels:

*Lenticel color.*—A light grey color (RHS Greyed Yellow Group 161 D).

*Density.*—Numerous lenticels are present, approximately 5 lenticels per $cm^2$.

*Size.*—Lenticels are approximately 1.5 millimeters in width and 2.5 millimeters long.

BRANCHES

Size: Current season shoots are considered medium for the variety. Mature branches, during the fourth year of production, are considered medium to large for the variety. Mature branches are pruned to a length of about 50.0 centimeters.

Diameter: Average as compared to other apricot varieties. The current season shoots have a diameter from 4.0 to 6.0 millimeters, and mature branches have a diameter from 20.0 to 25.0 millimeters.

Surface texture: Current season shoots have a smooth texture. Mature branches are medium rough. Roughness increases with tree age.

Crotch angles: The crotch angles are generally between 50 degrees and 70 degrees from the trunk axis. At maturity, the crotch angle increases with fruits weight. This particular characteristic is not considered distinctive of the variety, however.

Internode length: Generally between 15.0 millimeters and 20.0 millimeters.

Color of mature branches: Orange brown (RHS Greyed Orange 166 A) or green brown (RHS Brown N 200 B).

Color of current season's shoots: Considered an orange brown (RHS Greyed Orange Group 166 A to 166 B) on the upper part, whereas the lower part of new shoot tips is colored grey brown (RHS Grey Brown 199 A). The current season's shoots color evolves and turns to mature branches color when aging.

Vigor: Considered vigorous.

Lenticels:

*Density.*—Numerous lenticels are present, approximately 5 lenticels per $cm^2$, especially on mature branches.

*Size.*—Considered slightly smaller than trunk's lenticels, they are approximately 1.0 millimeters wide and 2.0 millimeters long.

*Color.*—A light grey (RHS Greyed Yellow Group 161 D).

LEAVES

Size: Considered medium for the species.

Leaf length: Approximately 83.0 to 90.0 millimeters.

Leaf width: Approximately 70.0 to 83.0 millimeters.

Leaf form: Almost circular.

Leaf tip form: Acuminate.

Leaf base form: Generally round or truncated.

Leaf margins: Considered crenate.

Thickness: Medium.

Upper surface texture: Smooth.

Lower surface texture: Smooth.

Leaf colour:

*Upper leaf surface.*—Green (RHS Green Group 137 A).

*Lower surface.*—A lighter green (RHS Green Group 137 C) than the upper leaf surface color.

Leaf venation: Pinnately veined.

Mid-vein:

*Thickness.*—Approximately 1.0 millimeter when measured at the base of the leaf.

*Color.*—Yellow green (RHS Yellow Green 145 A) near the apex and red violet (RHS Red Purple Group 59 B) from the middle of the mid-vein to its base.

Other veins color: Green (RHS Green Group 145 A to 145 B).

Uniformity: Leaves are of medium size and generally found alone. No stipules are generally found.

Leaf petioles:

*Size.*—Generally large.

*Length.*—Between 40.0 and 52.0 millimeters.

*Diameter.*—Approximately 1.5 millimeters.

*Surface.*—Generally smooth.

Petioles colour:

*Upper petiole surface.*—Depending on climatic conditions and sunlight exposure, the anthocyanic coloration on petiole's upper surface can be very present and varies from red (RHS Red Group 53 B) to purple red (RHS Red Purple Group 59 B).

*Lower surface.*—Light green, almost yellow (RHS Yellow Green 145 B to 145C).

Leaf glands:

*Size.*—Considered medium. Their length is about 1.0 millimeter and their width is about 1.0 millimeter.

*Length.*—Approximately 0.9 millimeters.

*Width.*—Approximately 0.9 millimeters.

*Number.*—Generally between 2 and 3 glands per leaf.

*Type.*—Round.

*Position.*—Alternate between upper portion of petiole and lower portion of leaf blade.

*Color.*—Generally greyed orange (RHS Greyed Orange Group 165 A).

Leaf stipules:

*Generally.*—No leaf stipules were observed.

FLOWERS

Flower buds:

*Generally.*—At pre-floral stage of development, the floral buds are conic in form with a very rounded tip (ball shaped). Their form is evolving until blooming, with variable dimensions. Just before blooming, floral buds are approximately 12.0 millimeters wide and approximately 20.0 millimeters long.

*Color.*—This characteristic is dependent upon the proximity to bloom. At pre-floral stage of development, the bottom of the flowers buds, formed by the sepals, is of purple-brown color (RHS Greyed Purple 183 B to 183 C); the corolla, formed by the petals, is generally of white color (RHS White Group N 155 B to N 155 C) with a slightly pink pigmentation (RHS Red Purple 69 C to 69 D).

Texture: Smooth.

Hardiness: The buds are considered hardy under typical central Pyrénées-Orientales department climatic conditions. No winter injury was noted during the last several years of evaluation in the central Pyrénées-Orientales department, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Pedicel:
*Length.*—About 3.0 millimeters.
*Width.*—About 1.5 millimeters.
Flower shoots of leaf buds:
*Form.*—Ovoid.
*Length.*—About 2.0 millimeters.
*Width.*—About 1.5 millimeters.
*Color.*—Orange grey (RHS Greyed Orange 175 A).
Flower shoots of flower buds:
*Form.*—Ovoid.
*Length.*—About 2.0 millimeters.
*Width.*—About 1.5 millimeters.
*Color.*—Orange grey (RHS Greyed Orange 175 A).
Date of bloom: Generally in March.
First bloom: The first bloom was observed on Mar. 6, 2003.
Full bloom: Mar. 10, 2003.
Petal fall: Mar. 15, 2003.
Blooming time: Considered semi-early season in relative comparison to other commercial apricot cultivars grown in the Pyrénées-Orientales department, France.
Duration of bloom: Between 8 and 12 days.
Flower size: Flower diameter at full bloom is approximately 23.0 to 28.0 millimeters.
Bloom quantity: Considered abundant, flowers are generally found in bunches.
Flower bud frequency: Generally 1 flower bud or several flower buds per groups of 2 to 3.
Petal size:
*Length.*—Generally about 12.0 millimeters.
*Width.*—Generally about 12.0 millimeters.
Petal form: Round-shaped, narrower at point of attachment.
Petal count: Generally 5, overlapping sepals.
Petal texture: Smooth.
Petal color: Generally, both sides of petals are colored in a very light pink (RHS Red Purple 69 B to 69 C) at popping stage and then white (RHS White Group N 155 B to N 155 C).
Fragrance: Moderate.
Petal claw color: Considered pale pink (RHS Red Purple N 66 D).
Petal margins: Generally slightly wavy, sinuate, with a smooth texture.
Petal base: Narrow at point of attachment.
Petal apex: Round.
Petal peduncle:
*Length.*—Approximately 3.0 millimeters.
*Diameter.*—Approximately 1.5 millimeters.
*Color.*—Generally yellow green (RHS Yellow Green 145 C) with areas colored almost in red (RHS Red 46 D).
Sepals:
*Size.*—Generally considered small.
*Sepal count.*—5.
*Form.*—Triangular, with a slightly pointed apex.
*Color.*—Considered purple brown (RHS Greyed Purple 183 B to 183 C).
*Margins.*—Smooth.
*Apex.*—The apex is round-shaped to slightly pointed.
*Texture.*—Smooth.
Stamens:
*Average number of stamen per flower.*—Approximately 35 stamens per flower.
*Length.*—Medium.
Filaments:
*Size.*—Approximately between 10.0 and 15.0 millimeters in length.
*Color.*—White (RHS White Group N 155 B).
Anthers:
*Color.*—Orange Yellow (RHS Yellow Orange 16 D).
Pistil:
*Number.*—Usually 1.
*Length.*—Approximately 20.0 to 21.0 millimeters including the ovary, which has a size of approximately 1.5 millimeters. Generally at the same level as anthers.
*Color.*—Considered a very pale green (RHS Yellow Green Group 150 D or RHS Yellow Green Group 151 D).
*Pubescence.*—Present.
Pollen:
*Pollen production.*—Pollen is abundant, and non autofertile.
*Color.*—Orange yellow color (RHS Yellow Orange 17 B to 17 C).
Filaments size: Approximately between 10.0 and 15.0 millimeters.
Calyx:
*Internal surface texture.*—Smooth.

FRUIT

Maturity: Considered medium-season, generally the first week of July.
Date of first picking: Jul. 3, 2003.
Date of last picking: Jun. 25, 2011. The date of harvest varies slightly with the prevailing climatic conditions. The 'ASF-COT0201 variety has medium date of picking and a grouped maturity. The maturity is grouped within 7 to 9 days and the harvest is generally performed in two runs.
Size:
*Generally.*—Considered large.
*Length.*—Approximately 50.0 to 55.0 millimeters.
*Width.*—Approximately 47.0 to 50.0 millimeters.
*Thickness.*—Approximately 48.0 to 52.0 millimeters.
Typical weight: Generally between 60.0 and 70.0 grams. This characteristic is highly dependent upon the prevailing cultural practices, and therefore is not particularly distinctive of the variety.
Fruit form:
*Generally.*—Round and very slightly elevated. The fruit is considered to be symmetrical.
Suture:
*Generally.*—Slightly marked, extending from the base to the apex. No apparent callousing or stitching exists along the suture line.
*Color.*—The suture has generally a color similar to the whole fruit color. The suture is colored with red orange (RHS Red Group 45 A to 45 B or RHS Red Group 45 B to 45 C).
Ventral surface:
*Form.*—Round.
Apex: Flat.
Base: Straight to slightly wide-mouthed.
Stem cavity: Shallow. Average depth of the stem cavity is about 4.5 millimeters. Average width is about 7.0 millimeters.
Stem:
*Size.*—Generally small. Stem length is about 5.0 to 6.0 millimeters. Stem diameter is about 2.0 millimeters.

*Color.*—Stem color is generally green (RHS Green Group 143 C to 143 D).

Fruit skin:

*Thickness.*—Considered medium.

*Texture.*—Smooth and strong.

*Pubescence.*—Present but very light, almost non-existent.

*Tendency to crack.*—None observed.

Color:

*Blush color.*—This blush color is an orange red (RHS Red Group 45 A to 45 B or RHS Red Group 45 B to 45 C). The orange red blush covers 40 to 60% of the fruit skin surface. The darker blush color within the described range appears on fruits exposed to sunlight. The percentage of the blush on the fruit skin surface can vary, and is generally dependant upon the prevailing conditions under which the fruit was grown.

*Ground color.*—The ground color covers 40 to 60% of the fruit skin surface, and is considered orange yellow (RHS Yellow Orange Group 17 A).

*Adherence to flesh.*—Very adherent.

*Taste.*—Very slightly acid, with a high level of sugars.

Flesh:

*Ripens.*—Homogenously.

*Texture.*—Fine and firm. Very melting and juicy at end of maturity.

*Fibers.*—Generally none observed.

*Aroma.*—Pronounced.

*Firmness.*—Firm and melting. Holds firmness over the time.

*Eating quality.*—Considered very good and aromatic, with a high level of sugars.

*Flavor.*—Considered very good. Good balance between sugar and acidity. Very aromatic.

*Juice.*—Very juicy. The juiciness increases with maturity.

*Brix.*—Generally superior to 15.0 degrees. This characteristic varies slightly with the number of fruit per tree, prevailing cultural practices and the surrounding climatic conditions.

*Flesh color.*—Considered medium orange (RHS Orange Group 16 A to 16 B or RHS Yellow Orange Group 22B).

STONE

Stone cavity:

*Color.*—Orange (RHS Orange Group 22 B).

*Length.*—Approximately between 27.0 and 30.0 millimeters.

Stone type: Free, but the stone seems to be slightly attached to the flesh through its base and its edges.

Size: Considered medium for the variety. The stone size varies depending upon the tree vigor, crop load and prevailing growing conditions.

*Length.*—Approximately 25.0 to 27.0 millimeters.

*Width.*—Approximately 20.0 to 22.0 millimeters.

*Diameter.*—Approximately 11.0 to 12.0 millimeters.

Stone form (viewed from stem end): Ovate, flattened.

Stone base shape: Round to slightly concave.

Stone apex shape: Round, generally no point is observed.

Stone surface:

*Surface texture.*—Medium to smooth.

*Ridges at stone surface.*—The ridges are present on both sides of the stone. A ridge is generally narrow. The ridges begin at the base and are extending all along the stone.

Stone color: The color of the dry stone is generally considered a greyed orange (RHS Greyed Orange 164 A to 164 B or RHS Greyed Orange 165 B to 165 C).

Tendency to split: Splitting is absent.

Kernel:

*Taste.*—Bitter.

*Length.*—Approximately 12.0 millimeters.

*Width.*—Approximately 13.0 millimeters.

*Thickness.*—Approximately 7.0 millimeters.

*Form.*—Ovate.

*Color.*—The kernel skin is a greyed orange (RHS Greyed Orange 165 B to 165 C). The almond, which is the seed of the kernel, is considered white (RHS White 155 D).

Use: The subject variety 'ASFCOT0201 is considered to be a apricot tree with a medium season maturity, and which produces fruits that are considered firm, attractively and luminously colored. Fruits have a balanced taste between acidity and sugar. They are excellent for uncooked or cooked consumption, melting and juicy when at full maturity. Fruits have excellent gustative qualities and are very aromatic. They are also useful for both local markets and very long distance shipping.

Keeping quality: Good. Fruits are well preserved during at least 3 weeks after harvest in a cold atmosphere. Fruits are considered to have a long shelf life after harvesting without alteration.

Shipping quality: Considered good. The fruit of the new apricot variety showed very little skin scarring or flesh bruises in picking, packing and shipping trials.

Resistance to insects and disease: No particular susceptibilities were noted. Under meticulous observations during planting, growing and harvesting of fruits, no particular resistance or sensitivity to plant or fruits diseases were noticed. Any variety, observed during indexing of plant characteristics, with abnormal fungus, bacterial virus or insect sensitivity is destroyed and eliminated from our breeding program.

Although the new variety of apricot tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of apricot tree as illustrated and described, characterized by fruits of very long shelf life without alteration after harvesting, and with a medium orange flesh of high eating quality, aromatic and with a high level of sugar, and with an attractive luminous orange red blush on a luminous orange yellow background.

* * * * *